US007538129B2

(12) United States Patent
Harran et al.

(10) Patent No.: US 7,538,129 B2
(45) Date of Patent: *May 26, 2009

(54) DIAZONAMIDE A ANALOG

(75) Inventors: Patrick G. Harran, Dallas, TX (US); Noelle Williams, Dallas, TX (US); Anthony Burgett, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 6 days.

This patent is subject to a terminal disclaimer.

(21) Appl. No.: 11/591,016

(22) Filed: Oct. 31, 2006

(65) Prior Publication Data

US 2007/0149583 A1 Jun. 28, 2007

Related U.S. Application Data

(63) Continuation-in-part of application No. 11/264,502, filed on Oct. 31, 2005.

(60) Provisional application No. 60/814,651, filed on Jun. 16, 2006.

(51) Int. Cl.
*A61P 35/00* (2006.01)
*A61K 31/425* (2006.01)
*C07D 291/00* (2006.01)

(52) U.S. Cl. ............................ 514/366; 514/375; 540/457

(58) Field of Classification Search ................ 514/366, 514/375; 540/457
See application file for complete search history.

(56) References Cited

U.S. PATENT DOCUMENTS 7,022,720 B2 * 4/2006 Harran et al. ................ 514/366
2003/0100589 A1 5/2003 Harran et al.

OTHER PUBLICATIONS

Ritter and Carreira, "The Diazonamides: The plot thickens," Angew Chem. Int. Ed. (2002) 41:2489-2495.
Wilson, "Total synthesis suprise: Scientists revise structure of coveted anticancer marine natural product," Dec. 21, 2001, Chemical and Engineering News, 79:11.
Li et al., "Synthetic seco forms of(−)-Diazonamide A," Angew Chem. Int. Ed. (2001) 40:2683-2685.
Li et al., "Total synthesis of nominal diazonamides—Part I: Convergent preparation of the structure proposed for (−)-diazonamide A," Angew Chem. Int. Ed. (2001) 40:4765-4769.
Li et al., "Total synthesis of nominal diazonamides—Part 2: On the true structure and origin of natural isolates," Angew Chem. Int. Ed. (2001) 40:4770-4773.
Nicolaou et al., "Construction of the complete aromatic core of diazonamide A by a novel hetero pinacol macrocyclic cascade reaction," Angew Chem. Int. Ed. (2001) 40:4705-4709.
Nicolaou et al., "Construction of the complete aromatic core of diazonamide A by a novel hetero pinacol macrocyclic cascade reaction," Angew Chem. (2001) 113:4841-4845.

Kreisberg et al., "Vilsmeier methodology for the synthesis of 3-(2-N-phtaloylacyl)indole derivatives, and its application to the synthesis of the GCDEF rings of diazonamide," Tetrahedron Lett. (2001) 42:627-629.
Vedejs et al., "Synthesis of the diazonamide core via a dieckmann-type cyclization," Org. Lett. (2001) 3:2451-2454.
Wipf et al., "Synthetic studies toward diazonamide A: a novel approach for polyoxazole synthesis," Org. Lett. (2001) 3:1261-1264.
Bagley et al., "Studies toward the synthesis of diazonamide A. Synthesis of the indole bis-oxazole flagment," Tetrahedron Lett. (2000) 41:6897-6900.
Bagley et al., "Studies toward the synthesis of diazonamide A. Synthesis of the 4-(oxazol-5-ylmethyl) aryltryptamine fragment," Tetrahedron Lett. (2000) 41:6901-6904.
Chan et al., "Synthesis of the 4-arylindole portion of the antitumor agent diazonamide and related studies," Tetrahedron Lett. (2000) 41:835-838.
Fuerst et al., "Synthesis of C(3) benzofuran-derived bisaryl quaternary centers: approaches to diazonamide A," Org. Lett. (2000) 2:3521-3523.
Lach et al., "Studies towards the synthesis of diazonamide A. Synthesis of a tyrosine-derived benzofuranone," Tetrahedron Lett. (2000) 41:6893-6896.
Magnus et al., "Synthesis of the dichlorobisoxazole-indole portion of the antitumor agent diazonamide by a putatie biogenetic strategy," Tetrahedron Lett. (2000) 41:831-834.
Nicolaou et al., "Model studies towards Diazonamide A:synthesis of the heterocyclic core," Angew Chem. Int. Ed. (2000) 39:3473-3478.
Nicolaou et al., "Model studies towards Diazonamide A:synthesis of the heterocyclic core," Angew Chem. (2000) 112:3615-3620.
Vedejs et al., "Atyrosin-derived benzofuranone related to Diazonamide A," Org. Lett. (200002:1031-1032.
Vedejs et al., "Progress toward synthesis of Diazonamide A. Preparation of a 3-(Oxazol-5-yl)-4-trfifluoromethyl-sulfonyloxylindole and its use in biaryl coupling reactions," Org. Lett. (2000) 2:1033-1035.
Belshaw et al., "Aminoacyl-CaAs as probes of condensation domain selectivity in nonribosomal pepetide synthesis," Science (1999) 284:486-489.
Hang et al., "The synthesis of 3-methoxylcarbonylbenzofuran-2(3H)-one derivatives via copper(I)-catalyzed coupling of o-bromophenols with dimethyl malonate," Synthesis (1999) 398-400.
Magnus et al., "Synthesis of benzofuranones related to Diazonamide via an intramolecular pummerer reaction," Tetrahedron Lett. (1999) 40:451-454.
Helene C. Vervoort, Ph.D. thesis, (1999) "Novel anticancer agents from Ascidiacea," University of California, San Diego (Scripps Institution of Oceanography).
Belshaw et al., "Kinetics and regioselectivity of peptide-to-heterocycle conversions by microcin B17 synthetase," Chem. Biol. (1998) 5:373-84.
Boto et al., "A synthetic approach towards the aromatic macrocyclic core of Diazonamide A based on $sp^2$-$sp^2$ coupling protocols," Tetrahedron Lett. (1998) 39:8167-8170.

(Continued)

*Primary Examiner*—Brenda L Coleman
(74) *Attorney, Agent, or Firm*—Morrison & Foerster LLP (57) ABSTRACT

A specific diazonamide A analog and its salts and conjugates are effective in treating proliferative diseases.

5 Claims, 4 Drawing Sheets

OTHER PUBLICATIONS

Jeong et al., "Macrocyclic triarylethylenes via Heck endocyclization: A system relevant to diazonamide synthesis," J. Org. Chem. (1998) 63:8640-8641.

Shu, "Recent natural products based drug development: A pharmaceutical industry perspective," J. Nat. Prod. (1998) 61:1053-1071.

Wipf et al., "Synthetic studies toward Diazonamide A. Preparation of the benzofuranone-indolyloxazole fragment," Tetrahedron Lett. (1998) 39:2223-2226.

Cragg, "Natural products in drug discovery and development," J. Nat. Prod. (1997) 60:52-60.

Moody et al., "Studies toward the synthesis of Diazonamide A. Unexpected formation of a 3, 4-bridged indole," J. Chem. Soc. Perkin. Trans. (1996) 16:2413-2419.

Takahashi et al., "Oxidative addition of 2-haloalkene to zirconocene," J. Am. Chem. Soc. (1995) 117:11039-11040.

Moody et al., "Synthesis of heterocyclic natural products: Model studies towards diazonamide A," Pure Appl. Chem. (1994) 66:2107-2110.

Gelfand and Bershadsky, "Microtubule dynamics: mechanism, regulation and function," Ann. Rev. Cell Biol. (1991) 7:93-116.

Lindquist and Fenical, "Isolation and structure determination of Diazonamides A and B, unusual cytotoxic metabolites from the marine ascidian Diazona chinesis," J. Am. Chem. Soc. (1991) 113:2303-2304.

Lindquist, Ph.D. thesis, University of California San Diego, 1989.

Negishi et al., "Reaction of zirconocene dichloride with alkyllithiums or alkyl grignard reagents as convenient method for generating a 'zirconocene' equivalent and its use in zirconium-promoted cyclization of alkenes, alkynes, dienes, enynes and diynes," Tetrahedron Lett. (1986) 27:2829.

International Search Report for PCT/US06/42565, mailed on Sep. 25, 2007, 2 pages.

Written Opinion of the International Searching Authority for PCT/US06/42565, mailed on Sep. 25, 2007, 5 pages.

* cited by examiner

DIAZONAMIDE A ANALOG

RELATED APPLICATIONS

This application is a continuation in part of U.S. application Ser. No. 11/264,502 filed 31 Oct. 2005, and claims benefit of priority to U.S. Ser. No. 60/814,651 filed 16 Jun. 2006. The contents of these documents are incorporated herein by reference in their entirety.

TECHNICAL FIELD

The invention relates to an analog of diazonamide A that has superior antitumor activity. A synthetic route to this compound is also disclosed.

BACKGROUND ART

Diazonamide A is a mitotic spindle-disrupting agent first isolated from the marine organism *Diazona angulata*. Numerous attempts have been made to synthesize this compound and its analogs. PCT publication WO 03/106438 describes a putative synthetic route; however, the structure of diazonamide A provided in that publication is incorrect. U.S. Pat. No. 7,022,720 ('720) correctly discloses the structure of diazonamide A and describes the synthesis of some of its analogs through the combined use of catalytic Heck endocyclization, stereo-controlled ring-contracting pinnacol rearrangement, and indole arylation via internal photo-induced electron transfer. Generic structures of some analogs are provided. A daughter application claiming priority from this patent was filed 31 Oct. 2005 and is published as 2006/0089397 and includes the structure of the analog, Compound J, claimed herein. The '720 patent does not specifically describe the compound of the present invention, which has surprisingly potent anti-mitotic activity.

DISCLOSURE OF THE INVENTION

The present invention is directed to a compound of the formula (Compound J) and the pharmaceutically acceptable salts thereof. The invention is also directed to pharmaceutical compositions containing this compound and/or its salts, to modified forms of this compound coupled to stabilizing or targeting agents, and to methods of treating proliferative diseases, in particular Taxol™-resistant cancers, using these compounds and formulations.

In another aspect, the invention is directed to methods to synthesize Compound J and its salts.

MODES OF CARRYING OUT THE INVENTION

Compound J has been shown, as described in the examples below, to have potent anti-mitotic activity with respect to certain cancers, in particular cancers that are resistant to Taxol™. Compound J can be supplied in its free base form, or can be supplied as a pharmaceutically acceptable salt, or as a mixture of the depicted form and the corresponding salt. Suitable salts include those of inorganic acids such as hydrochlorides, hydrobromides, sulfates, hydrosulfates, and the like, or organic acid addition salts such as the acetates, formates, maleates, and the like.

In addition, Compound J may be coupled to moieties such as targeting agents. Among such targeting agents are antibodies or immunologically active fragments thereof, including single-chain antibody forms directed against tumor antigens or against receptors or integrins associated with tumors, peptidomimetics directed against these moieties, and the like. In addition, Compound J may be coupled to an excipient such as polyethylene glycol for altering pharmacokinetics.

The formulations useful in the invention include standard formulations such as those set forth in *Remington's Pharmaceutical Sciences*, latest edition, Mack Publishing Co., Easton, Pa., incorporated herein by reference. Such formulations include those designed for oral delivery, slow release, topical administration, parenteral administration, or any other suitable route as determined by an attending physician or veterinarian. Thus administration may be systemic or local. Suitable vehicles or excipients include liposomes, micelles, nanoparticles, polymeric matrices, buffers, and the full range of formulations known to practitioners.

Compound J is particular useful in treating proliferative diseases, in particular, tumors and malignancies associated with breast, ovary, lung, colon, prostate, melanoma, colon, pancreas, glioma, carcinoma, and the like.

The formulations that include Compound J and/or its salt and/or its conjugates may also be used in combination with other drugs, such as additional antitumor agents or other palliative compounds such as compounds that aid in nutrition or general health.

Compound J is conveniently synthesized by treating the free amino precursor with S-2,5-dioxopyrrolidin-1-yl-2-hydroxy-3-methylbutanoate. This converts the free amine to the 3-methyl-2-hydroxybutylate.

Those skilled in the art will appreciate that this coupling reaction can also be accomplished with other activated esters of the 2-hydroxy3-methylbutanoate, such as by way of example only N-hydroxybenzotriazole ester, perfluorophenyl ester, N-hydroxyphthalimide esters, activated esters generated by the reaction of the carboxylic acid with a carbodiimide, and other activated esters conventionally used for acylation of an amine to form amide bonds; thus the invention provides a method to prepare Compound J by coupling an activated 2-hydroxy-3-methylbutanoate derivative, which may optionally be protected at the 2-hydroxyl, with the above described amine. The amine may also optionally be in protected form, i.e. it may have protecting groups on either or both of the indole nitrogen and the indoline nitrogen. Suitable protecting groups for use on the hydroxyl include acyl groups, silyl groups, pyran acetals, and the like. Suitable protecting groups for use on the ring nitrogen atoms of the amine compound, which are not intended to react with the hydroxybutanoate activated ester, may include acyl groups such as carbamates or trifluoroacetate, as well as silyl groups. Suitable protecting groups and methods to attach and remove them are well known in the art, and are described, for example, in T. H. Greene, PROTECTIVE GROUPS IN ORGANIC SYNTHESIS, $2^{nd}$ ed.

The following examples are offered to illustrate but not to limit the invention. Examples 1-16 describe the synthesis of Compound J. Examples 17-20 describe its biological activity.

EXAMPLE 1

7-Bromoindole

2-Bromonitrobenzene (1.10 kg, 5.45 mol) was dissolved in tetrahydrofuran (10 L) at room temperature. This solution cooled with stirring in a bath maintained at −78° C. When the internal temperature reached −40° C., vinylmagnesium bromide (16.3 L, 16.3 mol) was added at such a rate as to maintain the internal temperature at −40° C. during the addition. Upon complete addition, the reaction was removed from the bath and allowed to warm slowly to −30° C. over the course of 45 minutes. This required occasional cooling. The −30° C. reaction solution was quenched by rapid addition of a slightly cool (~10° C.) solution of saturated aqueous $NH_4Cl$ (10 L). Slight foaming occurred. (Inverse quench into the ammonium chloride solution is also satisfactory.) This resulted in a biphasic mixture with some undissolved magnesium salts in the form of a gel. The mixture was stirred for 30 minutes and separated. The aqueous layer was back extracted with tetrahydrofuran (10 L). The combined organic layers were evaporated at reduced pressure with a bath temperature of 35° C. and the resulting dark oil was taken up in methylene chloride (5 L) and dried with $Na_2SO_4$. The mixture was filtered and concentrated. The resulting material was chromatographed, eluting with 2% ethyl acetate-hexanes to give 7-bromoindole (557 g, 52% yield) of as an off-white solid. $^1H$ NMR ($CDCl_3$): consistent with proposed structure.

EXAMPLE 2

2-Acetamido-3-(7-bromo-1H-indol-3-yl)Propanoic Acid

To a 5 L, 3-neck round bottom flask, equipped with stir bar, nitrogen atmosphere, thermocouple and condenser, was added the title compound of Example 1 (252.1 g, 1.29 mol) followed by acetic acid (1.5 L) and acetic anhydride (760 mL, 8.04 mol). L-serine (266.9 g, 2.53 mol) was charged after stirring for 20 min. This mixture was stirred for 4h before it was heated to 40° C. After most of the solids had dissolved, the reaction was heated to 90° C., followed by an excursion to 110° C. The reaction was then cooled to 80° C., stirred at this temperature, and the reaction progress was monitored by HPLC. After 5 hours the reaction was complete as judge by the absence of 7-bromoindole in the chromatogram. The heat was removed, and the reaction was allowed to continue stirring overnight at room temperature.

Methanol (450 mL) was added and the reaction was concentrated in vacuo at ~50° C. to a thick, black tar. Methanol (3 L) was added to the residue and after vigorous agitation most of the residue went into solution, leaving behind a fine precipitate. To this mixture was added of $H_2SO_4$ (52.5 mL), and the reaction was stirred at reflux overnight. The reaction was cooled to room temperature and diluted with tetrahydrofuran (3 L). The solution was charged to a 12 L separatory funnel containing saturated aqueous $NaHCO_3$ (4 L). This mixture was extracted with methyl t-butyl ether (3×4 L). The organic layers were combined and washed with brine and dried over $Na_2SO_4$, then concentrated in vacuo to afford a mixture of brown solid and brown oil. Methylene chloride (500 mL) was added to the crude product, and some white solids remained undissolved. These crystals were filtered to afford ~10 g of product. Seed crystals were added to the filtrate, and after 30 minutes, a brown solid had precipitated. The new mixture was filtered, and more seed crystals were added to produce a third crop of precipitate, and this third mixture was also filtered. Addition of seed crystals to the filtrate produced no additional product. The filtrate was concentrated in vacuo to afford a brown foam, which was redissolved in methylene chloride (600 mL). Methyl t-butyl ether (MTBE) (1,250 mL) was slowly added to the solution, which precipitated a brown solid. The mixture was filtered, and the filtrate was added to other impure samples, then purified by column chromatography, eluting with methylene chloride-hexanes. None of the fractions containing product were very pure (range: 50%-75%), so all were recrystallized with MTBE to afford pale yellow powders. These samples were combined with the recrystallization samples to afford the title compound (139 g, 33% yield, 75% purity). $^1H$ NMR ($CDCl_3$): consistent with proposed structure.

EXAMPLE 3

Methyl 2-amino-3-(7-bromo-1H-indol-3-yl)Propanoate Hydrochloride $H_2SO_4$ (340 mL) was added slowly to a stirred mixture of the title compound of Example 2 (342 g, 1.05 mol) in methanol (3.4 L). The resulting dark brown mixture was heated to reflux for 16 hours at which time HPLC analysis indicated completion of the reaction. The reaction was cooled to room temperature and quenched slowly into a stirred mixture of water (4.8 L), sodium bicarbonate (342 g) and methylene chloride (4.8 L). Stirring was continued for 1.5 hours. The layers were separated and the aqueous layer was back extracted twice with methylene chloride (3.0 L). The combined extracts were dried with sodium sulfate and concentrated to a black tar. The material was dissolved in methylene chloride (3.0 L). 1N HCl in diethyl ether (1.1 L) was added slowly with external cooling. The suspension was cooled to ice bath temperature and filtered. The solids were washed twice with methylene chloride (500 mL) and three times with hexanes (500 mL). The solids were dried to constant mass in a vacuum oven at 32° C. to give the title compound (267.4 g, 76% yield). $^1$H NMR (CDCl$_3$): consistent with proposed structure.

EXAMPLE 4

Methyl 2-((S)-2-(benzyloxycarbonylamino)-3-methylbutanamido)-3-(7-bromo-1H-indol-3-yl)Propanoate The title compound of Example 3 (256.6 g, 770 mmol), TBTU (296.4 g, 1.2 eq) and Cbz-L-valine (212.7 g, 1.1 eq) were dissolved in dimethylformamide (DMF, anhydrous, 2,700 mL) and cooled to 0° C. for 30 min. Diisopropylethylamine (DIEA, 268 mL) was added slowly and the solution was allowed to warm to room temperature. Stirring was continued for 4 hours at which time HPLC indicated completion of reaction. The reaction was diluted with ethyl acetate (11 L) and water (7.5 L). The mixture was stirred for 1 hour and allowed to separate. The organic layer was washed once with water (7.5 L), twice with brine (7.5 L) and twice with saturated NaHCO$_3$ (7.5 L). The material was dried with sodium sulfate and concentrated to brown black solid. The material was taken up in methylene chloride (7.5 L) and combined with 22.2 g of another lot of similar quality material and silica gel (400 g). The solvent was removed to support the crude compound on silica. This material was divided in half and each half was chromatographed on a 6 in×4 ft silica gravity column. Each was eluted with methylene chloride (20 L) followed by 5% acetone in methylene chloride (20 L) followed by 8% acetone in methylene chloride (30 L) to give the title compound (383 g, 89% yield). $^1$H NMR (CDCl$_3$): consistent with proposed structure.

EXAMPLE 5

Methyl 2-((S)-1-(benzyloxycarbonylamino)-2-methylpropyl)-5-(7-bromo-1H-indol-3-yl)oxazole-4-carboxylate Dichlorodicyanoquinone (340.8 g, 1,500 mmol) was added to a stirred solution of the title compound of Example 4 (361.4 g, 681 mmol) dissolved in tetrahydrofuran (15 L) and heated to reflux for 6 hours at which time HPLC indicated complete reaction. The reaction was concentrated to ¼ its volume and diluted with ethyl acetate (12 L). The resulting black solution was washed three times with saturated aqueous NaHCO$_3$ (5.5 L). The organic layer was dried over sodium sulfate and concentrated to give the title compound as a black solid (392 g, 100% yield). $^1$H NMR (CDCl$_3$): consistent with proposed structure.

EXAMPLE 6

Methyl 2-((S)-1-amino-2-methylpropyl)-5-(7-bromo-1H-indol-3-yl)oxazole-4-carboxylate Hydrobromide

To 33% HBr in acetic acid (1.33 L) was added the title compound of Example 5 (403.4 g, 766 mmol) and the stirred vigorously for 1 hour and 20 min. The mixture was slowly and carefully added to MTBE (12 L) with external cooling and strong agitation. The mixture was stirred for 1 hour at 0° C. and filtered under N$_2$. The hygroscopic solids were washed with MTBE (1 L) and dried to constant mass in a vacuum oven to yield the title compound (277.5 g, 76.5%) as a fine brown solid. $^1$H NMR (CDCl$_3$): consistent with proposed structure.

EXAMPLE 7

Methyl 2-((S)-1-((S)-2-(benzyloxycarbonylamino)-3-(4-hydroxyphenyl)propanamido)-2-methylpropyl)-5-(7-bromo-1H-indol-3-yl)oxazole-4-carboxylate To diisopropylethylamine (225 mL, 1,290 mmol) stirred at 0° C. was added a solution of the title compound of Example 6 (277.5 g, 586.5 mmol), Cbz-L-tyrosine (194.2 g 615.9 mmol) and TBTU (207.2 g, 1.1 eq) in dimethylformamide (anhydrous, 2.77 L). The reaction was allowed to warm to room temperature and stirred for 16 hours at which time HPLC indicated completion of reaction. The reaction solution was slowly poured into saturated aqueous NaHCO$_3$ (12.0 L) and stirred for 30 min. The precipitate was filtered and the filter cake was thoroughly washed with water. The resulting brown material was dried to constant mass in a vacuum oven at 40° C. to yield the title compound (435 g). The title compound was further purified by recrystallization. The title compound was dissolved in isopropanol (9.0 L) at 70° C. The insoluble material was removed by filtration and the filtrate was heated while slowly adding hexanes (9.0 L). The suspension was allowed to cool to room temperature at which time an ice bath was applied. Once cooled the mixture was stirred at ice bath temperature for 30 min and filtered. The solid was washed with hexanes and dried to constant mass at 40° C. in a vacuum oven giving pure title compound (264 g, 61% yield). $^1$H NMR (CDCl$_3$): consistent with proposed structure.

EXAMPLE 8

The title compound of Example 7 (45.0 g, 65 mmol) was dissolved in tetrahydrofuran (325 mL) and was added rapidly to a −20° C. solution of PhI(OAc)$_2$ (20 g, 62 mmol) and LiOAc (12.7 g, 196 mmol) in 2,2,2-trifluoroethanol (13.0 L). The solution was stirred at −20° C. for 25 minutes at which time solid NaHCO$_3$ (117.5 g) was added. The cold bath was removed and stirring was continued for an additional 30 min. The mixture was filtered at 10° C. and the filtrate was concentrated. The residue, 94.6 g, was taken up in CHCl$_3$-tetrahydrofuran (3:1, 300 mL) and sonicated for 10 minutes. The precipitated undesired diastereomer was removed by filtration and the filtrate was concentrated to give crude title compound. The above operations were performed a total of 3 times to give a combined total of 223.6 g of crude title compound. The crude title compound was initially purified by silica plug filtration eluting with 100% ethyl acetate. This resulted in 179.9 g of material which was further purified by multiple column chromatography. A first column was eluted using 6:1 methylene chloride-tetrahydrofuran. This resulted in 71.1 g of material, which was taken up in 6:1 methylene chloride-tetrahydrofuran (200 mL) and refrigerated over- night. The precipitated undesired diastereomer was removed by filtration and the filtrate was concentrated to give 66.6 g of compound. This material was chromatographed for an additional 2 times eluting with 15:1 methylene chloride-tetrahydrofuran to give the title compound in two fractions: (16.8 g and 9.3 g). $^1$H NMR (DMSOd-6): consistent with proposed structure. Mass spectrum (ESI) m/z: 687 (M+1).

EXAMPLE 9

To a flask containing the compound synthesized in Example 8 (102 mg, 0.148 mmol) was added methanol (3.6 mL). The solution was cooled in ice-water bath for 15 minutes. A stock solution of LiOH in water (35.4 mg/0.6 mL, 1.48 mmol) was added dropwise at 0° C. The mixture was warmed to room temperature (all precipitate dissolved) and stirred for 4 hours. Less than 1% of the starting material remained after checking by LCMS. About 10 g of ice was added to the reaction mixture and the temperature was decreased to 0° C. Aqueous HCl (1N, 1.6 mL) was added dropwise at 0° C. to adjust the pH of the reaction mixture to between 2 and 3. Ethyl acetate (2×20 mL) was used to extract the desired acid. The combined organic layers were washed with water (10 mL), brine (10 mL) and dried over $Na_2SO_4$. The solution was concentrated to afford 100 mg of the title compound which was used in next step without further purification. $^1$H NMR (DMSOd-6): consistent with proposed structure.

EXAMPLE 10

To a dry flask containing the compound synthesized in Example 9 (100 mg) was added 2-amino-1-(7-hydroxy-1H-indol-3-yl)ethanone hydrochloride (50.3 mg, 0.222 mmol) and anhydrous DMF (0.5 mL). Triethylamine (31 μl, 0.222 mmol) was added at room temperature under $N_2$. A pre-made yellow solution of DHOBt (8.45 mg, 0.0518 mmol), EDCHCl (42.6 mg, 0.222 mmol) and triethylamine (31 μl, 0.222 mmol) in anhydrous DMF (2.0 mL) was added to the solution at room temperature. The mixture was stirred at 41 to 42° C. under $N_2$ for 6 hours. The reaction mixture was diluted with ethyl acetate (30 mL) followed by washing with water (10 mL), 10% aqueous $NaHSO_4$ (10 mL), water (2×10 mL), saturated aqueous $NaHCO_3$ (10 mL), water (2×10 mL), and brine (10 mL). The solution was dried over $Na_2SO_4$, filtered and evaporated to give the title compound (130 mg). $^1$H NMR (DMSOd-6): consistent with proposed structure.

EXAMPLE 11

To a dry flask containing the compound synthesized in Example 10 was added anhydrous tetrahydrofuran (0.9 mL) and $CH_2Cl_2$ (2.7 mL). The resulting solution was cooled in ice-water bath for 15 minutes. Acetic anhydride (42 ul, 0.444 mmol) and pyridine (18 ul, 0.222 mmol) were added at 0° C. Then the mixture was warmed to room temperature and stirred for 3.5 hours under $N_2$. The reaction was monitored via LCMS. The reaction solution was diluted with ethyl acetate (30 mL) followed by washing with water (10 mL) and brine (10 mL) and drying over $Na_2SO_4$. After concentration, 136 mg of crude product was obtained. Flash chromatography, eluting with ethyl acetate/$CH_2Cl_2$, 30/70~35/65) afforded the title compound (80 mg, 61% overall yield over the last three steps). $^1$H NMR (DMSOd-6): consistent with proposed structure.

EXAMPLE 12

Triphenylphosphine (474 mg, 1.81 mmol) and hexachloroethane (428 mg, 1.81 mmol) were added to a dry flask equipped with stir bar. Anhydrous $CH_2Cl_2$ (18.5 mL) was added and the resulting solution was cooled well in ice-water bath under $N_2$. Triethylamine (351 ul, 2.52 mmol) was added slowly to the solution, followed by stirring for 10 minutes at 0° C. The solution of the compound synthesized in Example 11 (160 mg, 0.180 mmol) in anhydrous CH$_2$Cl$_2$ (9.5 mL) was added dropwise and the temperature was kept at 0° C. to 2° C. After addition, reaction mixture was stirred at 0° C. for 10 minutes (total time should be less than 15 minutes). Water (34 μL) was added to quench the reaction. All solvent was evaporated at 15° C. under reduced pressure. Ethyl acetate (5 mL) was added to precipitate triphenylphosphine oxide. After filtering, the filtrate was concentrated again and the procedure above was repeated twice to remove additional triphenylphosphine oxide. The filtrate was concentrated followed by purification via flash chromatography eluting with ethyl acetate-toluene (60:40) to yield the title compound (110 mg, 70% yield.) $^1$H NMR (DMSOd-6): consistent with proposed structure.

EXAMPLE 13

The solution of the compound synthesized in Example 12 in acetonitrile (10.0 mg/4 mL) was added to a quartz test tube followed by sparging with N$_2$ for 30 minutes. A stock degassed solution of LiOH in H$_2$O (0.596 mg/0.60 mL) was added dropwise. The reaction solution turned dark yellow and was degassed with N$_2$ for 30 minutes. The quartz test tube was placed in photoreactor illuminated with 300 nm light bulbs. The reaction solution was radiated for 45 minutes and sparged with N$_2$. This reaction was repeated 12 times. The combined reaction mixtures were diluted with ethyl acetate (200 mL) followed by washing with sat. NH$_4$Cl (50 mL), H$_2$O (50 mL), brine (50 mL) and drying over Na$_2$SO$_4$ to give the title compound.

EXAMPLE 14

To a dry flask containing the compound synthesized in Example 13 (0.150 mmol) was added dry K$_2$CO$_3$ (61 mg) and anhydrous DMF (4 mL). A solution of 4-nitrophenyl trifluoromethanesulfonate in anhydrous DMF (61 mg/1.3 mL) was added to the reaction mixture at room temperature. The resulting yellow-brown solution was stirred at room temperature under N$_2$ for 1 hour. Then the mixture was diluted with ethyl acetate (100 mL) followed by washing with saturated aqueous NH$_4$Cl (2×20 mL), H$_2$O (5×20 mL), brine (2×20 mL) and dried over Na$_2$SO$_4$. After concentration, the product was purified via flash chromatography, eluting with ethyl acetate-CH$_2$Cl$_2$ (30:70) to afford the title compound (50 mg, 38% overall yield for the last two steps). $^1$H NMR (DMSOd-6): consistent with proposed structure.

EXAMPLE 15

To a flask containing the compound synthesized in Example 14 (50 mg, 0.057 mmol) was added MeOH (5 mL) and triethylamine (29 μL, 0.205 mmol) followed by purging with N$_2$. Then Pd(OH)$_2$/C (95 mg) was added under N$_2$. A balloon filled with hydrogen gas was added immediately and the flask was purged with hydrogen 4 times. The reaction was allowed to proceed for 3 hours. The mixture was filtered through a pad of Celite and the residue was washed by MeOH (2×10 mL). The filtrate was concentrated and diluted with ethyl acetate (50 mL). The solution was washed with H$_2$O (3×10 mL) and brine (10 mL), and dried over Na$_2$SO$_4$. After concentration, the title compound was obtained (33 mg); it was used in the next step without further purification.

EXAMPLE 16

To synthesize compound J of formula (1) shown above, to a dry flask containing the compound synthesized in Example 15 (2 mg, 0.0469 mmol) was added anhydrous tetrahydrofuran (1.1 mL). A solution (S)-2,5-dioxopyrrolidin-1-yl 2-hydroxy-3-methylbutanoate (11.1 mg, 0.0516 mmol) in anhydrous tetrahydrofuran (0.3 mL) was added to the reaction mixture at room temperature. The reaction mixture was stirred at room temperature under N$_2$ for 2 hours. The reaction mixture was diluted with CH$_2$Cl$_2$ (50 mL) followed by washing with sat. NaHCO$_3$ (2×5 mL), H$_2$O (5 mL) and brine (5 mL), and drying over Na$_2$SO$_4$. After concentration, the final product was purified via flash chromatography, eluting with MeOH—CH$_2$Cl$_2$ (3:9) to afford the title compound (19 mg, 58% yield). Mass spectrum (ESI) m/z: 697.2 (M+1). $^1$H NMR (DMSOd-6): consistent with proposed structure.

EXAMPLE 17

Inhibition of Various Cell Lines by Compound J

Figure 1:
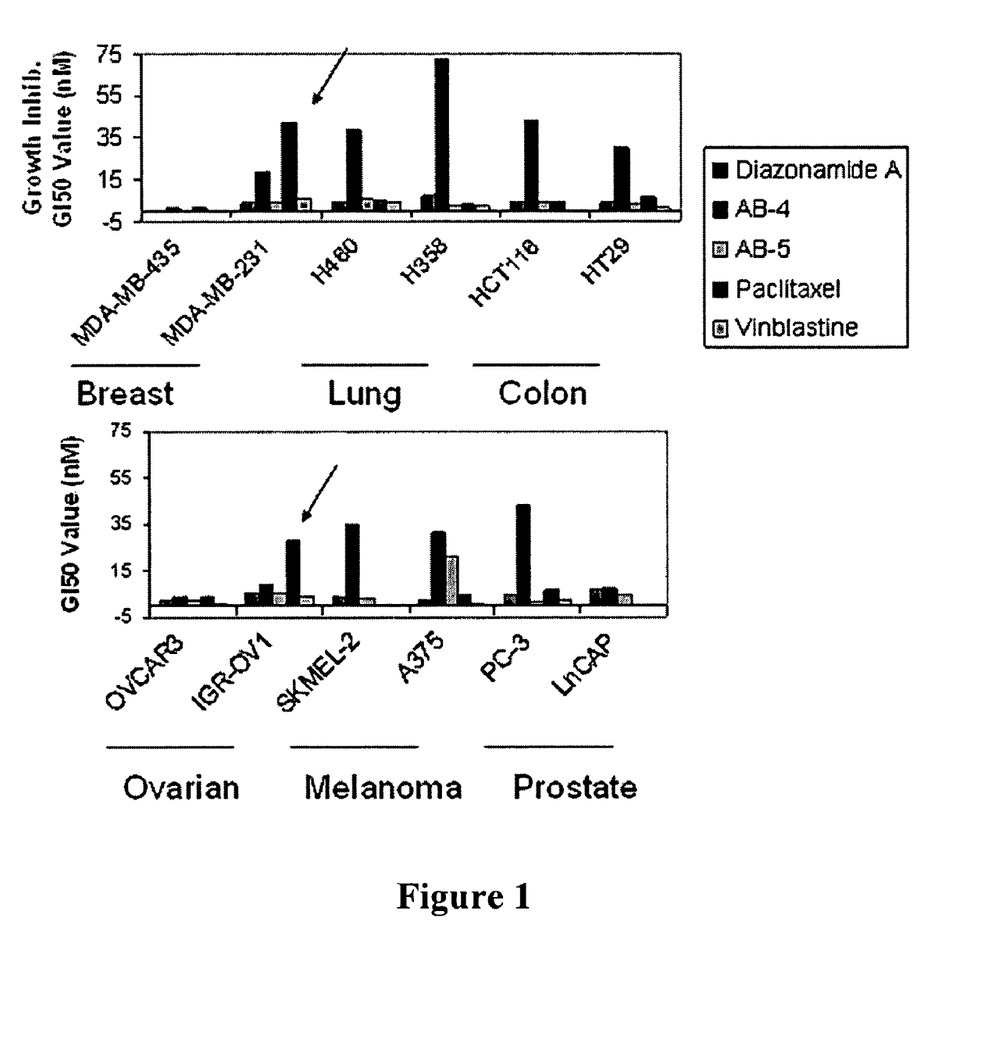
FIG. 1 shows the ability of Compound J to inhibit the growth of various cancer cell lines in comparison to diazonamide A, a hydroxylated form of Compound J., paclitaxel, and vinblastine.

A number of tumor cell lines representing breast, lung, colon, ovarian and prostate cancer as well as melanoma were assayed under standard growth conditions in presence of varying amounts of diazonamide A, a hydroxylated form of Compound J, Compound J, paclitaxel and vinblastine. The results are graphed as the concentration that diminishes growth by a factor of two (GI$_{50}$) in FIG. 1. In the box shown in FIG. 1, AB-4 is the hydroxylated form of Compound J and AB-5 is Compound J. As shown, all drugs tested had very low GI$_{50}$ concentrations in the breast tumor cell line MDA-MB-435 but diazonamide A, Compound J and vinblastine were more effective than the remaining drugs with respect to MDA-MB-231. In lung and colon, the hydroxylated form of Compound J was less effective than the remaining drugs. All of the drugs tested had very low (single-digit nM) GI$_{50}$'s in the ovarian cell line OVCAR3 but paclitaxel was significantly less effective than the remaining four drugs against the ovarian cell lines IGR-OV1 and SKMEL-2. In melanoma, Compound J and its hydroxylated form were less effective than the remaining drugs, but in the prostate cell lines PC-3 and LnCAP, all drugs performed well. (The hydroxylated form of Compound J was less active against PC-3.)

Figure 2:
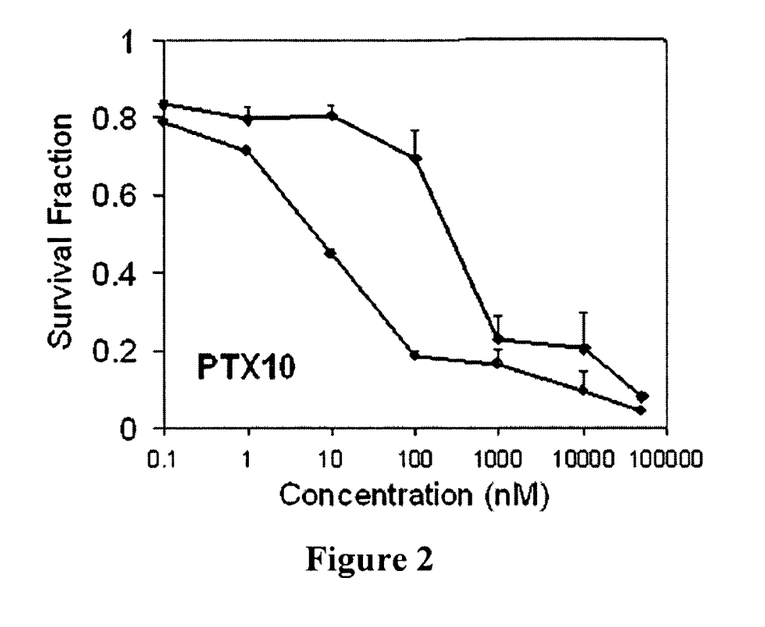
FIG. 2 shows a plot of survival fraction against concentration of drug with respect to PTX10 ovarian cancer cell lines for Compound J and paclitaxel.

Additional experiments testing the effect of Compound J and paclitaxel on the survival of PTX10ovarian tumor cell line are shown in FIG. 2. Plotted against concentration added, these results show that Compound J is more effective than paclitaxel in lowering the percentage of cells surviving. In FIG. 2, the circles represent Compound J and the diamonds represent paclitaxel.

EXAMPLE 18

Pharmacokinetics

Figure 3:
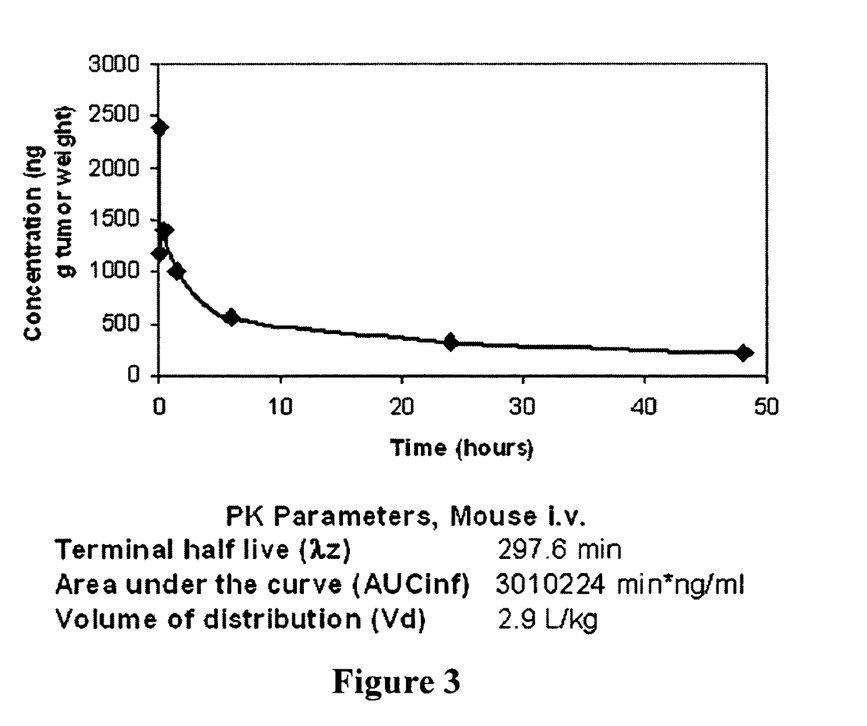
FIG. 3 is a graph showing the pharmacokinetics of Compound J.

Compound J was injected intravenously into mice containing xenograft tumors grown from MDA-MB-435 breast cancer cells. The intratumoral concentration of Compound J was measured as a function of time. The results are shown in FIG. 3. As summarized, the terminal half-life of this compound is 297.6 minutes, the area under the curve is 3010224 min*ng/ml and the volume of distribution is 2.9 l/kg.

EXAMPLE 19

Activity in vivo

Figure 4A:
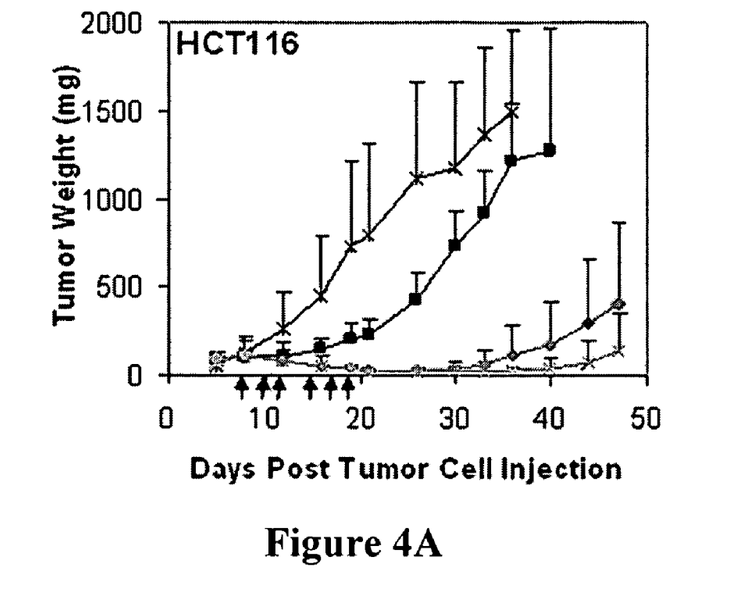
FIGS. 4A and 4B show the effect of Compound J as compared to paclitaxel on xenografts of HCT116 and PC-3 cells.
Figure 4B:
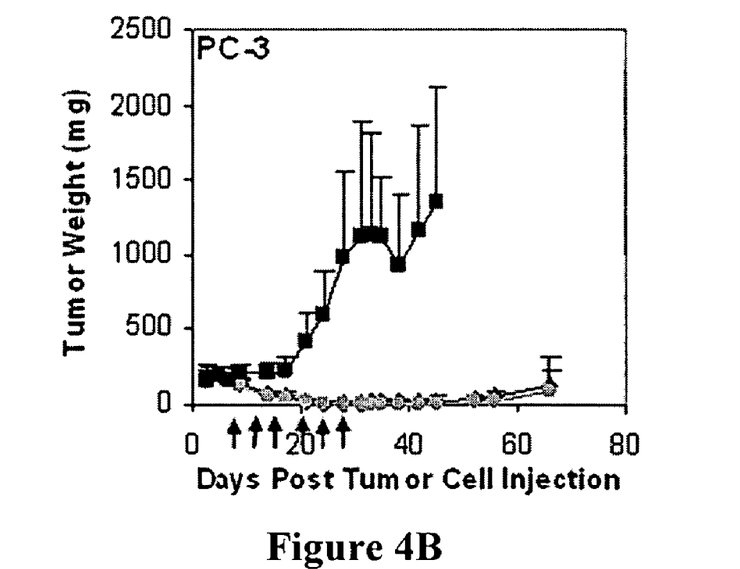

As shown in FIGS. 4A and 4B, Compound J is comparable to paclitaxel in inhibiting the growth of HCT116 xenografts and PC-3 xenografts.

Details of the preparation of murine models containing xenografts of HCT116 cells or PC-3 cells are described in the section following these examples. After the tumors were grown, therapy utilizing Compound J or paclitaxel was initiated. As shown in FIG. 4A, 20 mg/kg of Compound J administered IV slows tumor growth in a manner similar to paclitaxel at the same concentration. In FIG. 4A, the *'s represent control mice, the squares represent 5 mg/kg Compound J; the diamonds represent 20 mg/kg Compound J; and the slanted line represents 20 mg/kg paclitaxel. As seen, paclitaxel and Compound J at similar concentrations give similar curves of growth inhibition. In addition, four of 10 animals used in the study were free of tumors for over five months and experienced no weight loss.

In a similar model using PC-3 cells as the xenograft, again 20 mg/kg of either Compound J or paclitaxel significantly inhibited tumor growth. In FIG. 4B, the squares are the control, the dark circles are the data-points for Compound J and the light diamonds are data-points for paclitaxel.

EXAMPLE 20

Effect on Neutrophil Proliferation and Cell Counts

Figure 5A:
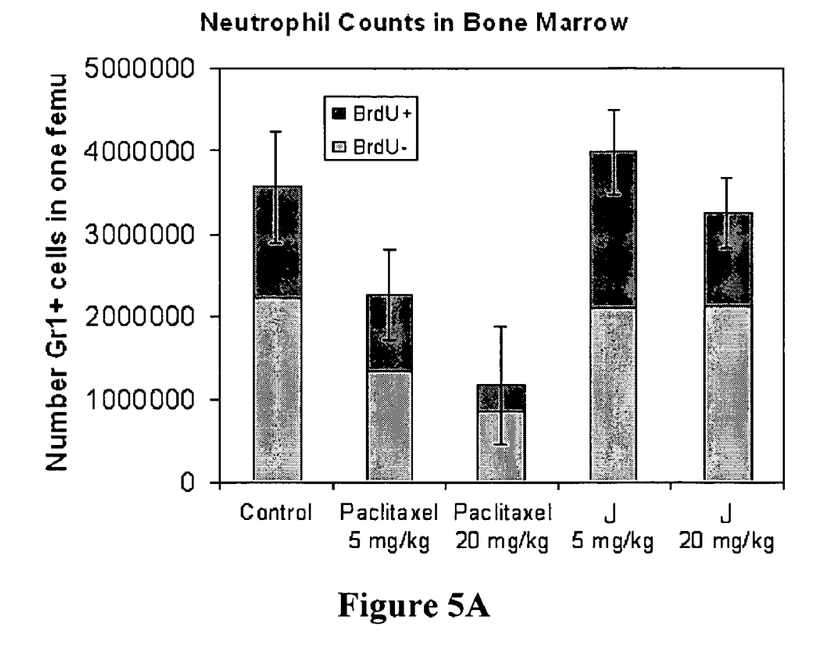
FIGS. 5A and 5B show that Compound J has no effect on neutrophil proliferation or cell counts in vivo.
Figure 5B:
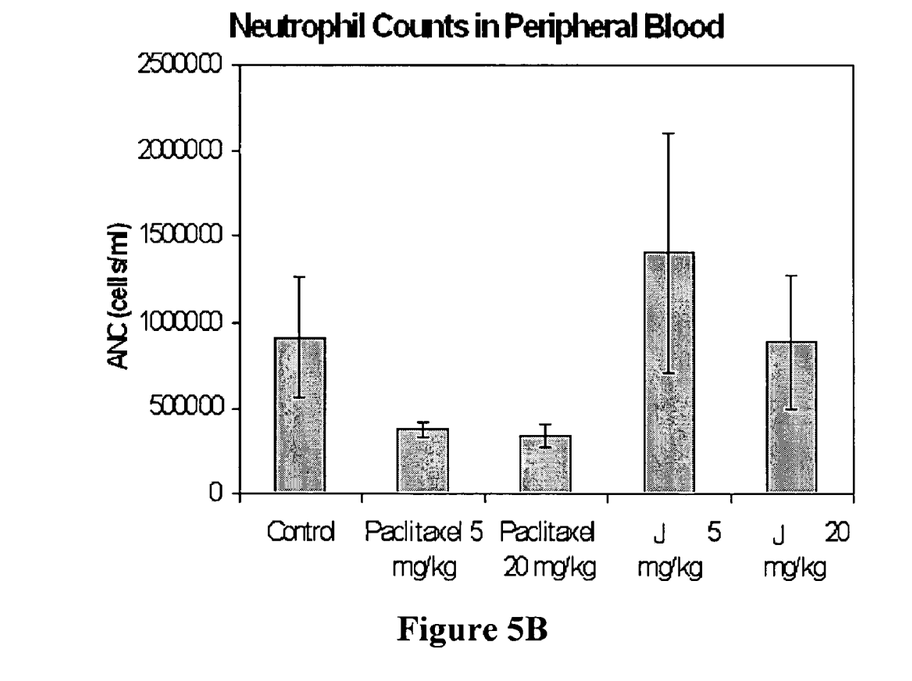

As shown in FIG. 5, although paclitaxel results in a reduction of neutrophil counts in bone marrow and in peripheral blood at dosages of 5 mg/kg and 20 mg/kg, Compound J at these concentrations has no effect on these cell counts.

In addition to measuring the affect on tumors, the effect of paclitaxel and Compound J on neutrophils in blood marrow and blood were obtained. As shown in FIG. 5A, although paclitaxel at 20 mg/kg significantly lowered neutrophil counts in bone marrow, a comparable dose of Compound J had no effect. The data are provided as the number of GR1+ cells in one femu.

In FIG. 5B, similarly, the neutrophil count in peripheral blood is greatly lowered by both 5 mg/kg and 20 mg/kg of paclitaxel, but is not significantly affected by similar amounts of Compound J. These data are tabulated as ANC (cell/ml).

The data obtained for growth inhibition in xenografts for Compound J as compared to paclitaxel is shown below.

TABLE 1

SUMMARY OF COMPOUND J EFFICACY DATA

| Tumor | Compound | Delivery Route | % Max T/C$^a$ | Log$_{10}$ Tumor Cell Kill$^b$ | #Tumor Free (day) |
|---|---|---|---|---|---|
| HCT116 | Compound J (20 mg/kg) | IV | 0.2 | 1.8 | 2/5 (243+) |
| (colon) | Compound J (5 mg/kg) | IV | 26.5 | 0.54 | 0/5 |
|  | Compound J (5 mg/kg) | IP | 41.9 | 0.37 | 0/5 |
|  | Paclitaxel (20 mg/kg) | IV | 0.2 | 3.2 | 1/5 (243+) |
| PC3 | Compound J (20 mg/kg) | IV | 0.3 | 3.4 | 2/5 (157+) |
| (prostate) | Paclitaxel (20 mg/kg) | IV | 0 | 3.4 | 4/5 (157+) |
| MDA-MB-435 | Compound J (20 mg/kg) | IP | 6.8 | 0.6 | 0/6 |
| (breast) | Vinblastine (0.7 mg/kg) | IP | 14.1 | 0.6 | 0/6 |
| MDA-MB-435 | Compound J (20 mg/kg) | IP | 3.1 | 1.0 | 0/6 |

TABLE 1-continued

SUMMARY OF COMPOUND J EFFICACY DATA

| Tumor | Compound | Delivery Route | % Max T/C[a] | Log$_{10}$ Tumor Cell Kill[b] | #Tumor Free (day |
|---|---|---|---|---|---|
| (breast) | Vinblastine (0.7 mg/kg) | IP | 41.1 | 0.2 | 0/6 |
| HCT116 | Compound J (20 mg/kg) | IP | 9.3 | 1.0 | 0/5 |
| (colon) | Vinblastine (0.45 mg/kg) | IP | 56.0 | 0.2 | 0/5 |

% Max T/C = median treated tumor weight/median control tumor weight
Log$_{10}$ Tumor Cell Kill = [(T − C) × 0.301]/Td
T = time in days for treated group to reach 300 mg
C = time in days for control group to reach 300 mg
Td = tumor doubling time The details of the protocol for Examples 19 and 20 are as follows:

Materials Required:
PC3 prostrate tumor cells and HCT116 colon tumor cells (acquired from the tumor repository Division of Cancer Treatment and Diagnosis (DCTD) of the NCI
Complete RPMI Media
  RPMI (Cat# 11875-085, Invitrogen)
  10% Heat-inactivated (30' 56° C.) Fetal Bovine Serum (Cat# 100-106, Gemini Bio-Products
  2 mM L-glutamine (Cat# 25030-081, Invitrogen)
  0.1 mM MEM Non-Essential Amino Acids Solution (Cat#11140-050, Invitrogen)
  10 U/ml Penicillin/10 μg/ml Streptomycin (Cat#15140-122, Invitrogen)
  1 mM Sodium Pyruvate (Cat#1 1360-070)
Trypsin-EDTA (Cat#25300-054, Invitrogen)
Ca$^{2+}$/Mg$^{2+}$-free Phosphate Buffered Saline, 5% dextrose in water
Cell Culture Dish 150 mm×25 mm (Cat# 430599, Coming, Inc.)
10 and 25 ml pipets, standard pipet-aid, p200 and p1000 pipette tips and standard pipetmen
Athymic NCr-nu/nu nude mice at 6-12 weeks of age, either sex (Strain code: 01B74, NCI Frederick Animal Production Program—suppliers include Charles River Labs and Taconic Farms). Female mice of approximately 7 weeks of age were utilized for existing experiments.
Standard 1 cc tuberculin syringe, 30G½ and 25G⅝ needles (Becton Dickinson)
Falcon 5 ml tubes (Cat#352054)
50 and 15 ml disposable plastic conical tubes (Falcon or similar vendor)
Trypan Blue Solution (0.4%) (Cat#T8154, Sigma)
Hausser phase contrast hemacytometer (Cat# 02-671-54, Fisher)
Ice bucket
Balance for weighing mice (accurate to 0.2 g)
Vernier calipers
Vivarium facility free from known pathogens (nude mice should be housed in isolation from conventional mice if possible—separate rooms or micro-isolator cages equipped with individual air flow; all animal housing, bedding, water should be autoclaved prior to use; standard irradiated mouse chow should be used; animals should be changed out of cages within laminar flow hood; investigators handling mice should be suitably garbed—disposable gown, bonnet, booties, gloves, mask)
AB-5 (Compound J) compound
Ethyl alcohol, 200 proof (Aaper, MFD 041205)
Cremaphor (Cat# C5135, Sigma)
Paclitaxel (Cat#ANP0010, Polymed Therapeutics)

Procedure:
1) Rapidly thaw PC3 or HCT116 cells (if necessary) in 37° C. water bath. Transfer contents to 9ml complete RPMI media. Spin 5' at 1200 rpm (240 Xg). Discard media and resuspend pellet in 8 ml complete RPMI media. Plate in 100 mm×25 mm cell culture dish in 5% CO2, 37° C. humidified incubator.
2) Allow to grow for 5-10 days, splitting (aspirate media, wash with 3-5 ml PBS, add 1 ml trypsin-EDTA, incubate 3-5' at 37° C., add media to desired volume and transfer to multiple plates) 1:8 to 1:10 every 3-4 days as necessary to allow cells to enter phase of logarithmic growth.
3) When cells are growing well, begin to expand to 150 mm×25 mm dishes. We use 20 ml of media in a 150 mm dish and use 2 ml of trypsin for splitting. When nearly confluent, there should be 2×10$^7$ cells/150 mm dish.
4) Plan ahead to time arrival of nu/nu mice such that they can acclimate to animal facility for 1 week prior to injection of tumor cells. During this time, ear tag or mark in accord with standard practice for vivarium).
5) Harvest PC3 or HCT116 cells when you anticipate having sufficient cells for total number of mice in study (Total number of mice=7 mice/group×total #groups—suggested groups: vehicle control, Paclitaxel positive control, AB-5+ up to 5 additional mice to allow for variation in take rate of xenograft; i.e. 26 mice). Plan to inject 10 million cells/mouse and allow for loss of cells/volume during injection process. That is, if 30 mice are to be injected, plan to harvest cells sufficient for at least 35 injections—35×10 million cells=3.5×10$^8$ cells. In the existing HCT116 experiment, 7.5×10$^6$ cells were injected per mouse. Five mice per group were utilized for AB-5 treatment and four mice per group were utilized for the control and paclitaxel treatments. In the existing PC3 experiment, 10$^7$ cells were injected. Six mice per group were utilized for the control treatment and five mice per group were utilized for the AB-5 and paclitaxel treatments. Smaller group sizes were necessary due to limitations in AB-5 availability.
6) Harvest cells as for splitting in steps 2 and 3 above. It is helpful to harvest only 10 plates at a time and place harvested cells on ice as one will need to process a large number of plates for a single experiment. Wash plates with additional media 1-2 times in addition to media used to dilute trypsin and harvest cells initially. Cells from 10 plates with associated washes will comfortably fit in one 50 ml conical. All steps should be conducted using aseptic technique and cells and centrifuge should be kept cold throughout procedure.

7) Once all cells have been harvested, spin down. 5' 1200 rpm (240×g). Resuspend pellets in 5-10 ml of plain (serum- and additive-free) RPMI. Pool pellets and then count pooled cell population diluted to concentration suitable for counting. Count 50 µl+50 µl trypan blue on a standard hemacytometer. Spin down cells as before and repeat serum-free wash an additional two times to ensure complete removal of serum. It may be helpful to divide cells back into multiple 50 ml conical tubes for counting and washes, but be sure to pool back into a single tube for final spin.

8) Resuspend cell pellet, taking into account volume of pellet itself, at $4\times10^7$/ml in serum free media. Pipeting or gentle vortexing is acceptable.

9) Take cells on ice to vivarium where mice should be already in cages ready for injection.

10) Draw up 0.8-0.9 ml of cells into 1 cc tuberculin syringe. Attach 25G needle and carefully knock out bubbles so that 0.7 ml of cells remain in syringe ready to inject. Leave remaining cells on ice.

11) Manually restrain mice with left hand, holding tail and skin behind the head firmly so mouse cannot move, but is still capable of breathing. Wipe skin to be injected with alcohol wipe and pull up an area of loose skin. With bevel up on needle, gently insert syringe and needle containing cells just under the skin of the mouse and slowly inject 0.2 ml of cells ($1\times10^7$ cells). Area of injection should form a raised area under the skin. Replace mice in cages.

12) Begin measurements of tumor size with vernier calipers (measure length and width and calculate volume as $(L\times W^2)/2$ three days following injection. Also measure mouse weight. In general, mouse weights should be measured at the same time every day (within 1-2 hours) to avoid expected daily fluctuation. Measure tumor volume at least one additional time at 2-3 day intervals to make sure tumor volume is increasing. Therapy can be initiated when tumor volume is between 150-250 mm³. This point should be reached within 5-10 days of initial injection. Do not use mice whose tumors fall significantly out of this range. Therapy was initiated 5 days after injection of tumor for the existing PC3 experiment and 8 days after injection of tumor for the existing HCT116 experiment.

13) Prior to first day of therapy, aliquot paclitaxel and AB-5/Compound J compounds into individual dose aliquots. It should be possible to estimate weight of mice on first day of therapy based on weights measured during initial tumor growth period. Aliquot sufficient compound per tube for the number of mice in treatment group+1.5-2 extra doses. Both paclitaxel and Compound J are given at 20 mg/kg. To minimize compound loss and maximize accuracy, we weigh 20-30 mg of compound and dissolve in ethanol. Aliquots of desired compound amount are then pipetted into individual tubes and dried down under vacuum. Aliquots are stored desiccated at −20° C. in Teflon or glass tubes.

14) On the first day of therapy, randomly group mice such that the average tumor volume per group is consistent. If using males, multiple cages may need to be utilized as it is inadvisable to re-group male nu/nu mice with new nu/nu mice because of fighting.

15) Prepare a stock solution of 1:1 cremaphor:ethanol. Prepare Compound J and paclitaxel for injection by first dissolving in 20 µl/dose cremaphor:ethanol with vigorous vortexing or sonnication as necessary. Dilute in 5% dextrose such that final concentration of cremaphor:ethanol is 10% (i.e. add 180 µl of 5% dextrose per dose). Vortex to mix. Solution will be slightly viscous. Paclitaxel may require slightly higher concentration of excipient to remain in solution (up to 20% final). In the existing HCT116 and PC3 experiments, 20% excipient was utilized for the paclitaxel formulation and 10% for the AB-5 formulation.

16) Warm tail using a 150 W heat lamp. We choose to warm only the tail but standard techniques used by vivarium are fine. Place mouse in Tailveiner. Wipe vein with alcohol wipe and slowly inject 0.2 ml over 5 seconds.

17) Six doses should be given at an interval of every other day (q2d×6). In the existing HCT116 and PC3 experiments, doses were given Mon/Wed/Fri for two weeks (q2-3d×6).

18) Mice should be weighed and dose recalculated for each dose.

19) Tumor volume and weight should be measured every 3-4 days (Monday/Friday) for several months following tumor injection. Control mice should reach 20 mm in longest diameter (point necessitating sacrifice at our facility) within 30-40 days. Both paclitaxel and Compound J should cause significant regression with cures in 40-80% of mice.

What is claimed is:

1. A compound of the formula

(I)

or a pharmaceutically acceptable salt or conjugate thereof.

2. The compound of claim 1 in the form of a pharmaceutically acceptable salt.

3. A pharmaceutical composition which comprises as active ingredient the compound of claim 1 or a salt thereof and further includes a pharmaceutically acceptable excipient.

4. A method to synthesize a compound of the formula:

which method comprises treating a compound of the formula:

or a protected form thereof having a protecting group in place of a hydrogen on at least one ring nitrogen,
with an activated ester of (S)-2-hydroxy-3-methylbutanoic acid or a protected form thereof having a protecting group on the 2-hydroxyl group;

followed by removal of any protecting groups that were present on the amine or the hydroxyl group.

5. The method of claim 4, wherein the activated ester of (S)-2-hydroxy-3-methylbutanoic acid is the N-hydroxysuccinimide ester of (S)-2-hydroxy-3-methylbutanoic acid, which is treated with a compound of formula:

to provide the product of formula:

* * * * *

UNITED STATES PATENT AND TRADEMARK OFFICE
CERTIFICATE OF CORRECTION

PATENT NO. : 7,538,129 B2  Page 1 of 1
APPLICATION NO. : 11/591016
DATED : May 26, 2009
INVENTOR(S) : Patrick G. Harran et al.

It is certified that error appears in the above-identified patent and that said Letters Patent is hereby corrected as shown below:

Col. 1, line 5 insert:

--This invention was made with grant support from NIH (RO1-GM6059103) and NSF (CHE-9984282). Thus, the government has certain rights in this invention.--

Signed and Sealed this

Twenty-sixth Day of October, 2010

David J. Kappos
*Director of the United States Patent and Trademark Office*